US006571230B1

(12) United States Patent
Parida

(10) Patent No.: US 6,571,230 B1
(45) Date of Patent: May 27, 2003

(54) METHODS AND APPARATUS FOR PERFORMING PATTERN DISCOVERY AND GENERATION WITH RESPECT TO DATA SEQUENCES

(75) Inventor: Laxmi P. Parida, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/478,551

(22) Filed: Jan. 6, 2000

(51) Int. Cl.[7] ........................... G06F 17/00; H03M 5/00
(52) U.S. Cl. ............................................. 706/48; 341/55
(58) Field of Search ............................... 706/48; 341/55

(56) References Cited

U.S. PATENT DOCUMENTS 5,977,890 A    11/1999   Rigoutsos et al. ............ 341/55

OTHER PUBLICATIONS

Wu et al, "Motif. Neural Network Design for Large–Scale Protein Family Identification", IEEE International Conference on Neural Networks, Jun. 1997.*
Gao et al, "Motif Detection in Protein sequences", IEEE International Workshop on Groupware String Processing and Information Retrieval Symposium, Sep. 1999.*
L. Parida et al., "Pattern Discovery on Character Sets and Real–valued Data: Linear Bound on Irredundant Motifs and an Efficient Polynomial Time Algorithm," Proceedings of the Eleventh Annual ACM–SIAM Symposium on Discrete Algorithms, pp. 297–308, 2000.
Yamaguchi et al., "Protein Motif Discovery from Amino Acid Sequence by Sets of Regular Patterns," Research Report of Information Processing Society, Information Processing Society, vol. 95, No. 76, 33–40, (Jul. 28, 1995). (English Translation).
Rigoutsos et al., "Bioinformatics; Combinational Pattern Discovery in Biological Sequences: the TEIRESIAS Algorithm," Oxford University Press, vol. 14, No. 1, 55–67 (1998).

L.A. Parida, "Algorithmic Techniques in Computational Genomics," Ph.D. thesis, Courant Institute of Mathematical Sciences, New York University, (1998).
A. V. Hoe et al., "Elementary Graph Algorithms," Data Structure and Algorithms, Addison–Wesley Publishing Company, Chapter 23, pp. 465–493, 1983.
R. Agrawal et al., "Fast Discovery of Association Rules," Advances in Knowledge Discovery and Data Mining, AAAI/MIT Press, Chapter 12, pp. 307–328, MA, 1995.
D. Gusfield, "Linear–Time Construction of Suffix Trees," Algorithms on Strings, Trees and Sequences: Computer Science and Computational Biology, Cambridge University Press, Chapter 6, pp. 94–119, New York, 1997.
Y. Gao et al., "Motif Detection in Protein Sequences," pp. 1–12, Apr. 16, 1999.
L.P. Parida, "Algorithmic Techniques in Computational Genomics," Ph.D. thesis, Courant Institute of Mathematcial Sciences, New York University, Part II, Sequence Analysis, Chapter 9, Pattern Discovery, pp. 130–142, Sep. 1998.
L. Parida et al., "An Approximation Algorithm for Alignment of Multiple Sequences Using Morif Discovery," Journal of Combinatorial Optimization, pp. 1–36, 1999.
L. Parida et al., "MUSCA: An Algorithm for Constrained Alignment of Multiple Data Sequences," Genome Informatics, pp. 1–15, 1999.

* cited by examiner

Primary Examiner—George B. Davis
(74) Attorney, Agent, or Firm—Ryan, Mason & Lewis, LLP; Casey P. August

(57) ABSTRACT

Given an input sequence of data, a motif is a repeating pattern. The data could be a sequence of characters or sets of characters or even real values. In the first two cases, the number of motifs could potentially be exponential in the size of the input sequence and in the third case there could be uncountably infinite number of motifs. By suitably defining the notion of maximality and redundancy for any sequence with n characters, there exists only a linear (or no more than 3n) number of special motifs and every other motif can be generated from these irredundant motifs.

21 Claims, 4 Drawing Sheets

METHODS AND APPARATUS FOR PERFORMING PATTERN DISCOVERY AND GENERATION WITH RESPECT TO DATA SEQUENCES

FIELD OF THE INVENTION

The present invention generally relates to data sequence processing methodologies and, more particularly, to methods and apparatus for discovering and generating motifs with respect to sequences of data such as, for example, sequences of characters, character sets and real numbers.

BACKGROUND OF THE INVENTION

Given an input sequence of data, a "motif" is a repeating pattern, possibly interspersed with don't-care characters, that occurs in the sequence. The data could be characters or sets of characters or real values. In the first two cases, the number of motifs could potentially be exponential in the size of the input sequence and in the third case there could be uncountably infinite number of motifs. Typically, the higher the self similarity in the sequence, the greater is the number of motifs in the data.

Motif discovery on such data, such as repeating DNA or protein sequences, is a source of concern since such data exhibits a very high degree of self-similarity (repeating patterns). Usually, this problem of an exploding number of motifs is tackled by pre-processing the input, using heuristics, to remove the repeating or self-similar portions of the input. Another way of trimming down the number of motifs is to use a "statistical significance" measure. However, due to the absence of a good understanding of the domain, there is no consensus over the right model to use.

Thus, there is a trend towards model-less motif discovery in different fields. To keep the problem manageable, it is useful to identify a small number of motifs that capture important information about the family of motifs. However, no conventional method exists which is able to satisfactorily identify a small enough number of such motifs to provide applications interested in utilizing the motifs with manageable and practical results.

SUMMARY OF THE INVENTION

The present invention provides methods and apparatus for detecting motifs in sequences of data, such as, for example, sequences of characters, character sets and real numbers, such as to provide applications interested in utilizing the motifs with manageable and practical results. Particularly, the invention provides that, for any sequence, there exists only a linear number of special motifs and every other motif can be simply generated from them. We name these special motifs "irredundant motifs." The result is meaningful also from an algorithmic viewpoint, since the ideas from the proof can be used to design a polynomial time algorithm to detect these irredundant motifs. This bound on the number of useful motifs gives validation to motif-based approaches, since the total number of irredundant motifs does not explode. This result is of significance to most applications that use pattern discovery as the basic engine such as data mining, clustering and matching. This family of irredundant motifs is also very characteristic of the family of all the motifs. For example, in applications such as multiple sequence alignment, we have shown that the irredundant motifs suffice to obtain the alignment. However, in applications that use the motifs to extract signature motifs of sets of sequences, all the motifs, including the redundant ones, may be of relevance.

In one illustrative aspect of the present invention, a method of detecting repeating patterns (i.e., motifs) in an input data sequence, wherein the data sequence includes elements from an element alphabet, comprises the steps of: (i) obtaining the input data sequence; (ii) constructing a set of patterns from the input data sequence, each pattern being unique and including one or more elements from the input data sequence, and each pattern having a list associated therewith representing the location of the pattern in the input data sequence; (iii) removing a pattern from the set when the location list of the pattern is a union of the location lists of at least two other patterns in the set; (iv) for each pair of compatible patterns in the set, constructing a new pattern which is a concatenation of the pair of compatible patterns, each new pattern having a location list associated therewith; and (v) storing the patterns, and associated location lists, remaining after the removing step and the new pattern constructing step as the detected repeating patterns. The one or more patterns may further include one or more don't care positions, i.e., don't care characters. As mentioned, the elements of the input data sequence may be in various forms, e.g., characters, character sets or real numbers.

In accordance with such a methodology, as will be explained below, no more than 3n repeating patterns are detected given an input data sequence which includes n elements. The no more than 3n repeating patterns are maximal and non-redundant, i.e., they are irredundant patterns or motifs. From these irredundant patterns, patterns that are non-maximal and/or redundant may be generated. In one embodiment, the non-maximal and/or redundant patterns are generated in accordance with one or more annotated tries.

In one exemplary application, as will be explained below, the input data sequence is a protein sequence and the inventive methodologies are used in accordance with protein sequence homology detection.

These and other objects, features and advantages of the present invention will become apparent from the following detailed description of illustrative embodiments thereof, which is to be read in connection with the accompanying drawings.

DETAILED DESCRIPTION OF PREFERRED EMBODIMENTS

Figure 1:
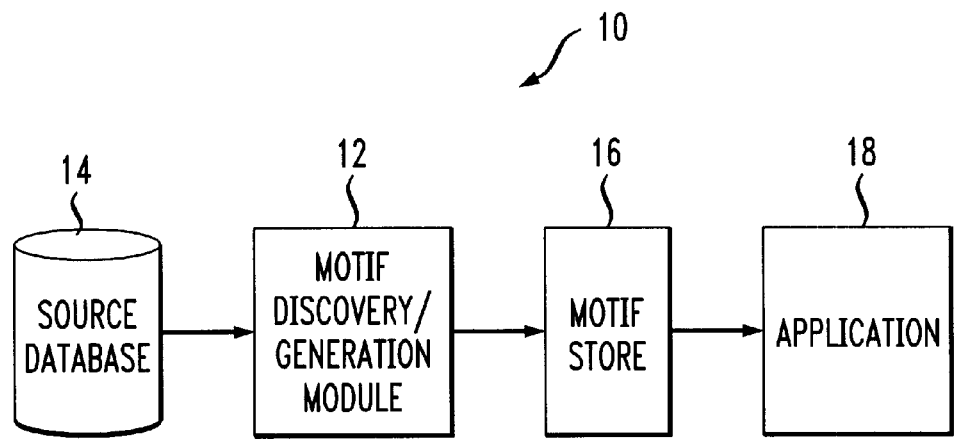
FIG. 1 is a block diagram illustrating a motif discovery and generation system according to one embodiment of the present invention.

Referring initially to FIG. 1, a block diagram of a motif discovery and generation system according to an-embodiment of the present invention is shown. The illustrative system 10 includes a motif discovery/generation module 12, a source sequence database 14 and a motif store 16. Also shown is an application 18, which is not necessarily part of the system, but which utilizes one or more of the motifs stored in store 16. Generally, the module 12 employs a pattern discovery or detection algorithm, to be explained in detail below, in order to discover irredundant motifs from data input from a source database 14, from which all other repeating patterns or motifs may then be generated. It is to be appreciated that the source database comprises data sequences from which repeating data patterns are discovered for use by one or more applications such as, for example, data mining, clustering or matching applications. The data sequences in the database may, for example, be in the form of sequences of discrete characters from a fixed character alphabet, sets of discrete characters from a fixed character alphabet, or sequences/sets of real numbers.

It is to be appreciated that another application which may implement the motif discovery and generation methodologies of the invention is deoxyribonucleic acid (DNA) or protein sequence homology detection. In such an application, a probe protein sequence may be submitted to a search engine system implementing the invention in order to check for k occurrences of the probe sequence in the database of protein sequences. The database is pre-processed in accordance with the motif discovery and generation methodologies of the invention to generate irredundant motifs. It is to be understood that the probe sequence is compared to the generated motifs. The resulting data may have varied applications. For example, it may be used to make a determination as to which sequences in the database the probe sequence is homologous. One of ordinary skill in the art will realize that such a search operation may be greatly improved, for example, from an accuracy and speed standpoint, by pre-processing the sequences in accordance with the methodologies of the invention described herein, prior to the search.

Figure 2:
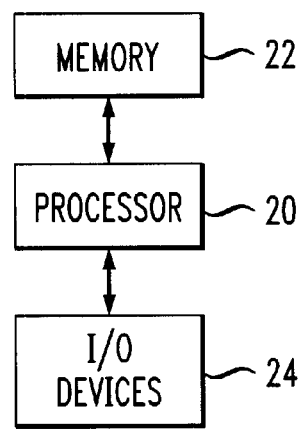
FIG. 2 is a block diagram illustrating a hardware implementation of a motif discovery and generation system according to one embodiment of the present invention.

FIG. 2 is a block diagram of an exemplary hardware implementation of the system 10 of FIG. 1. As shown, the system 10 may be implemented in accordance with a processor 20 a memory 22 and I/O devices 24. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, a fixed memory device (e.g., hard drive), a removable memory device (e.g., diskette), flash memory, etc. In addition, the term "input/output devices" or "I/O devices" as used herein is intended to include, for example, one or more input devices, e.g., keyboard, for entering sequences and/or other data to the processing unit, and/or one or more output devices, e.g., CRT display and/or printer, for presenting discovery results and/or other results associated with the processing unit. It is also to be understood that the term "processor" may refer to more than one processing device and that various elements associated with a processing device may be shared by other processing devices. Accordingly, software components including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

It is to be appreciated that, in an alternative embodiment, the invention may be implemented in a network-based implementation. That is the user may submit source data sequences (in lieu of a separately stored source database 14) at a remote client computer system, while the discovery module 12 resides and is executed on a server computer system in communications with the client via a network such as, for example, the Internet. The network could alternatively be a private network and/or a local network. Thus, a user operating remotely on his client computer system, e.g., a personal computer, laptop and/or some other type of personal processing device, enters data sequences through application software running on the computer system, e.g., web browsing software and/or a graphical user interface associated with the system. The sequences are passed over the network, in a conventional manner, and processed by server. The server receives the sequences and executes the methodologies of the invention in order to discover and/or generate motifs. The server then returns some or all of the results to the client via the network. It is to be understood that the server may include more than one computer system. That is, one or more of the elements in FIG. 1 may reside on and be executed by their own computer system, e.g., with its own processor, memory and I/O devices.

Given a general description of the elements of the motif discovery system of the invention and various exemplary hardware implementations, the various inventive methodologies will now be explained in detail.

For ease of reference, the remainder of detailed description will be divided into sections as follows: (I) Notation; (II) Notion of Redundancy; (III) Bounding the Irredundant Motifs; (IV) Algorithm to Detect the O(n) Irredundant Motifs; (V) Generating Redundant Motifs: Annotated Trie; (VI) Generalization; and (VII) Applications. Accordingly, in Section I, we define motifs and some basic related concepts (such as maximality); in Section II, we introduce the notion of irredundancy; and, in Section III, we show that the number of such motifs is only linear in the input length. In Section IV we describe a low polynomial time algorithm to extract the irredundant motifs; and, in Section V, we give a systematic and efficient way to compute all the redundant motifs. In Section VI, we extend our problem to dealing with input that is a sequence of sets instead of characters and also the case of sequence on real numbers. We conclude with examples of possible applications of the notion of redundancy and the polynomial time algorithm, in Section VII.

I. Notation

Let s be a sequence on an alphabet $\Sigma$, '.'$\notin \Sigma$. A character froth $\Sigma$, say $\sigma$, is called a solid character and '.' is called a "don't care" or "dot" character. For brevity of notation, if x is a sequence, then $|x|$ denotes the length of the sequence and if x is a set of elements then $|x|$ denotes the cardinality of the set. The jth ($1 \leq j \leq |s|$) character of the sequence is given by s[j].

Definition 1 ($\sigma_1 <, =, \leq \sigma_2$) $\sigma_1$ is a "don't care" character then $\sigma_1 < \sigma_2$. If both $\sigma_1$ and $\sigma_2$ are identical characters in $\Sigma$, then $\sigma_1 = \sigma_2$. If either $\sigma_1 < \sigma_2$ or $\sigma_1 = \sigma_2$ holds, then $\sigma_1 \leq \sigma_2$.

Definition 2 (p occurs at l, cover) A string, p, on $\Sigma \cup$ '.', occurs at position l in s if $p[j] \leq s[l+j]$ holds for $1 \leq j \leq |p|$. p is said to cover the interval $[l, l+|p|-1]$ on s.

Definition 3 (k-motif m, location list $\mathcal{L}_m$) Given a string s on alphabet $\Sigma$ and a positive integer k, $k \leq |s|$, a string m on $\Sigma \cup$ '.' is a k-motif with location list $\mathcal{L}_m = (l_1, l_2, \ldots, l_p)$, if all of the following hold:

1. $m[1], m[|m|] \in \Sigma$.

(The first and last characters of the motif are solid characters; if "don't care" characters are allowed at the ends, the motifs can be made arbitrarily long in size without conveying any extra information.)

2. $p \geq k$.

3. there does not exist a location $l, l \neq l_i$, $1 \leq i \leq p$ such that m occurs at l on s (the location list is of maximal size).

(This ensures that any two distinct location lists must correspond to distinct motifs.)

If m is a string on $\Sigma$, m is called a "simple motif." If m is a string of $\Sigma \cup \{`.`\}$, m is called a "rigid motif." In the rest of the discussion, a k-motif is referred to as a motif.

Consider s=ABCDABCD. Using the definition of motifs, the different 2-motifs are as follows:

1. $m_1$=AB with $\mathcal{L}_{m1}$={1, 5},
2. $m_2$=BC with $\mathcal{L}_{m2}$={2, 6},
3. $m_3$=CD with $\mathcal{L}_{m3}$={3, 7},
4. $m_4$=ABC with $\mathcal{L}_{m4}$={1, 5},
5. $m_5$=BCD with $\mathcal{L}_{m5}$={2, 6} and
6. $m_6$=ABCD with $\mathcal{L}_{m6}$={1, 5}.

Notice that $\mathcal{L}_{m1} = \mathcal{L}_{m4} = \mathcal{L}_{m6}$=and $\mathcal{L}_{m2} = \mathcal{L}_{m5}$. Using the notation $\mathcal{L}+i=\{x+i|x \in \mathcal{L}\}$, $\mathcal{L}_{m5}=\mathcal{L}_{m6}+1$ and $\mathcal{L}_{m3}=\mathcal{L}_{m6}+2$ hold. We call the motif $m_6$ "maximal" as $|m_6|>|m_1|$, $|m_4|$ and $|m_{5|>|m2|}$. Motifs $m_1$, $m_2$, $m_3$, $m_4$ and $m_5$ are non-maximal motifs.

We give the definition of maximality below.

Definition 4 (Maximal Motif) Let $p_1, p_2, \ldots p_k$ be the motifs in a sequence s. Let $p_i[j]$ be '.', if $j>|p_i|$. A motif $p_i$ is maximal if and only if there exists no $p_j$, $l \neq i$ and no integer $0<\sigma$ such that $\mathcal{L}_{pi}+\delta=\mathcal{L}_{pj}$ and $p_i[\delta+j] \leq p_j[j]$ hold for $1 \leq j \leq |p_i|$.

The definition ensures that the motif is maximal in composition, and maximal in length.

However, the notion of maximality alone does not suffice to bound the number of motifs. We now illustrate motivation of the need for defining irredundant maximal motifs by giving two simple examples of strings that have an unusually large number of maximal motifs without conveying extra information about the input.

EXAMPLE 1

Let the input string s have the following form:

$ac_1c_2c_3baXc_2c_3bYac_1Xc_3bYYac_1c_2Xb$

Then the maximal motifs (which are $2^{\Omega(\sqrt{n})}$ in number) are as follows.

Motif Location List

|  | [$ac_1c_2c_3b$ | $aXc_2c_3bY$ | $ac_1Xc_3bYY$ | $ac_1c_2Xb$] |
|---|---|---|---|---|
| a . . . b | + | + | + | + |
| a..$c_3$b | + | + | + |  |
| a.$c_2$.b | + | + |  | + |
| a$c_1$..b | + |  | + | + |
| a.c2$c_3$b | + | + |  |  |
| a$c_1$.$c_3$b | + |  | + |  |
| a$c_1c_2$.b | + |  |  | + |

It is to be understood that the '+' symbol in the tables herein refers to the locations in the input sequence where the motifs occur.

EXAMPLE 2

Let s=aaaaaaaaaa and k=2. By the definition, the motifs with the location lists shown as positions on the input string are as follows.

|  | location list |
|---|---|
| size motif | [a a a a a a a a a a] |
| 2 aa | + + + + + + + + + + |
| 3 aaa | + + + + + + + + + |
| 4 aaaa | + + + + + + + + |
| 5 aaaaa | + + + + + + + |
| 6 aaaaaa | + + + + + + |
| 7 aaaaaaa | + + + + + |
| 8 aaaaaaaa | + + + + |
| 9 aaaaaaaaa | + + + |
| 10 aaaaaaaaaa | + + |

In other words, a sequence of n identical characters has n−2 maximal motifs.

Consider a minor variation of the original string s'=aaaaaXaaaaa. Note that the number of motifs increase drastically. The motifs, in increasing order of size, along with the locations list are as follows. We also give the non-maximal motifs (for instance all the motifs of size 6) for the sake of completeness.

|  | [a a a a a X a a a a a] |
|---|---|
| Motif size = 2 |  |
| aa | + + + +  + + + + |
| Motif size = 3 |  |
| aaa | + + +  + + + |
| a.a | + + +  +  + + + |
| Motif size = 4 |  |
| aaaa | + +  + + |
| a.aa | + +  +  + + |
| aa.a | + +  +  + + |
| a..a | + +  + +  + + |
| Motif size = 5 |  |
| aaaaa | +  + |
| a.aaa | +  +  + |
| aa.aa | +  +  + |
| aaa.a | + +  + |
| a..aa | +  + +  + |
| a.a.a | +  +  +  + |
| aa..a | +  + +  + |
| a . . . a | +  + +  + |
| Motif size = 6 |  |
| a. .aaa | + + |
| aa. .aa | + + |
| aaa..a | + + |
| a.aa.a | +  + |
| a.a.aa | +  + |
| aa.a.a | + + |
| aa . . . a | + + + |
| a . . . aa | + + + |
| a.a..a | + +  + |
| a..a.a | + +  + |
| a . . . a | + + + |
| Motif size = 7 |  |
| a..aaaa | + + |
| a.a.aaa | + + |
| a.aa.aa | + + |
| a.aaa.a | + + |

-continued

|  | [a | a | a | a | a | X | a | a | a | a | a] |
|---|---|---|---|---|---|---|---|---|---|---|---|
| aa..aaa |  |  |  |  | + | | + |  |  |  |  |
| aa.a.aa | + |  | + |  |  | |  |  |  |  |  |
| aa.aa.a |  | + |  | + |  | |  |  |  |  |  |
| aaaa.aa |  |  |  |  | + | | + |  |  |  |  |
| aaa.a.a | + |  | + |  |  | |  |  |  |  |  |
| aaaa..a | + | + |  |  |  | |  |  |  |  |  |
| a . . . aaa |  |  |  |  | + | | + | + |  |  |  |
| a.a..aa |  |  | + | + |  | |  | + |  |  |  |
| a.aa..a | + |  | + |  |  | |  | + |  |  |  |
| a.a.a.a | + |  |  | + |  | |  | + |  |  |  |
| a..a.aa |  |  | + |  | + | |  | + |  |  |  |
| a..aa.a | + |  |  |  | + | |  | + |  |  |  |
| a....aa |  |  | + | + | + | | + |  |  |  |  |
| aa....a | + | + | + | + |  | |  |  |  |  |  |
| a.....a | + | + | + | + | + | |  |  |  |  |  |

Motif size = 8

| aa..aaaa |  |  |  |  | + | | + |  |  |  |  |
| aa.aa.aa | + |  |  |  | + | |  |  |  |  |  |
| aaa.a.aa | + |  | + |  |  | |  |  |  |  |  |
| aaaa..aa | + | + |  |  |  | |  |  |  |  |  |
| aaa..aaa |  |  |  | + |  | |  |  |  |  |  |
| aa.a.aaa |  |  | + |  |  | | + |  |  |  |  |
| aa.a..aa | + |  | + |  |  | |  | + |  |  |  |
| aa..a.aa | + |  |  |  | + | |  | + |  |  |  |
| aaa...aa | + |  | + | + |  | |  |  |  |  |  |
| aa . . . aaa |  |  |  | + | + | | + |  |  |  |  |
| aa....aa | + | + | + | + |  | |  |  |  |  |  |

Motif size = 9

| aaa.a.aaa | + |  |  | + |  | |  |  |  |  |  |
| aaaa..aaa | + | + |  |  |  | |  |  |  |  |  |
| aaa..aaaa |  |  |  | + |  | | + |  |  |  |  |
| aaa..aaa | + | + |  | + |  | |  |  |  |  |  |

Motif size = 10

| aaaa..aaaa | + | + |  |  |  | |  |  |  |  |  |

II. Notion of Redundancy

We saw in the last section an example where a small change in the input string (replacing just one character by another) increases the number of maximal motifs from linear to exponential. This suggests that using a notion stronger than maximality would be meaningful. However, the notion of redundancy needs to be meaningful as well. Informally speaking, we call a motif m redundant if m (and its location $\mathcal{L}_m$) can be deduced from the other motifs without studying the input string s. We introduce such a notion below and the section on "Generating operations" (Section II(a) below) describes how the redundant motifs and the location lists can be computed from the irredundant motifs.

Definition 5 ($m_1 \leq m_2$) Given two motifs $m_1$ and $m_2$ with $|m_1| \leq |m_2|$, $m_1 \leq m_2$, holds if $m_1[j] \leq m_2[j]$, $1 \leq j \leq |m_1|$.

For example, let $m_1$=AB..E, $m_2$=AK..E and $m_3$=ABC.E.G. Then $m_1 \leq m_3$, and $m_2 \leq m_3$.

The following lemmas are straightforward to verify.

Lemma 1 If in $m_1 \leq m_2$, then $\mathcal{L}_{m1} \supseteq \mathcal{L}_{m2}$.

Lemma 2 If $m_1 \leq m_2$ and $m_2 \leq m_3$, then $m_1 \leq m_3$.

Definition 6 (Redundant motif) A maximal motif m, with location list $\mathcal{L}_m$, is redundant if there exist maximal motifs $m_i$, $1 \leq i \leq p$, such that $\mathcal{L}_{m4} = \mathcal{L}_{m1} \cup \mathcal{L}_{m2} \ldots \cup \mathcal{L}_{mp}$ (i.e., every occurrence of m on s is already covered by one of the motifs $m_1, m_2 \ldots, m_p$).

Definition 7 (fixed-size redundant) A maximal motif m, with location list $\mathcal{L}_m$, is redundant if there exist maximal motifs $m_i$, $1 \leq i \leq p$, with $\mathcal{L}_m = \mathcal{L}_{m1} \cup \mathcal{L}_{m2} \ldots \cup \mathcal{L}_{mp}$, and $|m|=|m_i|$, $\forall i$ motif m is called "fixed-size redundant."

Definition 8 (Irredundant motif) A maximal motif that is not redundant is called an irredundant motif.

Notice that the notion of fixed-size redundancy is a little weaker than the general irredundancy as in Definition 8 since if a motif is fixed-size redundant, it is redundant but the converse is not true. We discuss the example of irredundancy after describing the generating operations.

(a) Generating Operations

The redundant motifs need to be generated from the irredundant ones, if required. We define the following generating operations. Let m, $m_1$ and $m_2$ be motifs.

1. Prefix operator, $P^\delta(m)$, $1 < \delta < |m|$.

This is a valid operation when $\delta$ is an integer and $m[\delta]$ is a solid character, since all the operations are closed under motifs. $P^\delta(m)$ is the string given by $m[1 \ldots \delta]$.

For example, if m=AB..CDE, then $P^3(m)$ is not a valid operation since m[3] is a dot-character (i.e., a don't care character). Also, $P^5(m)$=AB..C.

2. The following binary operations are valid only if $|m_1|=|m_2|$ and

For each i, $1 \leq i \leq |m_1|$, $m_1[i] \leq m_2[i]$ or $m_2[i] \leq m_1[i]$.

($.\oplus.$) $m=m_1 \oplus m_2$, where in is such that every solid-character in m is a solid-character in both $m_1$ and $m_2$ (i.e., $m[i]=m_1[i] \cap m_2[i]$), otherwise it is a dot-character. For example if $m_1$=A..D..G and $m_2$=AB...FG. Then, $m=m_1 \oplus m_2$=A . . . G.

($.\hat{\times}.$) $m=m_1 \hat{\times} m_2$, where m is such that every solid-character in m is a solid-character in at least one of $m_1$ and $m_2$ (i.e., $m[i]=m_1[i] \cup m_2[i]$), otherwise it is a dot-character. For example if $m_1$=A..D..G and $m_2$=AB...FG. Then, $m=m_1 \oplus m_2$=AB.D.FG.

The Operations Satisfy the Following Properties.

1. If $m=m \oplus m_2$, then $m \leq m_1$ and $m \leq m_2$.

If $m=m_1 \hat{\times} m_2$, then $m_1 \leq m$ and $m_2 \leq m$.

2. (symmetric)

$m_1 \hat{\times} m_2 = m_2 \hat{\times} m_1$.

$m_1 \hat{\times} m_2 = m_2 \hat{\times} m_2$.

3. (associative)

$m_1 \oplus (m_2 \oplus m_3) = (m_1 \oplus m_2) \oplus m_3$.

$m_1 \hat{\times} (m_2 \hat{\times} m_3) = (m_1 \hat{\times} m_2) \hat{\times} m_3$.

4. The $P^\delta$ operator distributes over $\oplus$, i.e., $P^\delta(m_1 \oplus m_2) = P^\delta(m_1) \oplus P^\delta(m_2)$.

These properties are straightforward to verify.

Returning to Examples 1 and 2 Consider Example 1 discussed in the last section. The motifs not in bold, in the example, are fixed size redundant. Each of the redundant motifs can be constructed from the motifs in the these using the generating operations. For example, a..c$_3$b = a.c$_2$c$_3$b $\oplus$ ac$_1$.c$_3$b and $\mathcal{L}_{a..c3b} = \mathcal{L}_{a.c2c3b} \cup \mathcal{L}_{ac1.c3b}$.

Consider Example 2. For a fixed size of the motif f, $2 \leq f \leq 10$, in this example, the motifs shown in italics are redundant with respect to the other motifs of the same size f. The location lists of these motifs may be checked to verify the redundancy of the motifs. The basis with respect to fixed-size redundancy consists of all the motifs shown in bold which is $O(n^2)$ in number. However, a basis using the general notion of redundancy for the input string is shown below. To compare it with the basis for the original string s, we reproduce the basis for s as well.

| size motif | s' = aaaaaXaaaaa |
|---|---|
| | [a a a a a X a a a a a] |
| 2 aa | +  +  +  +     +  +  +  + |
| 3 aaa | +  +  +        +  +  + |
| 4 aaaa | +  +           +  + |
| 5 aaaaa | +              + |
| 7 a.aaa.a | +        + |
| 8 aa.aa.aa | +        + |
| 9 aaa.a.aaa | +     + |
| 10 aaaa..aaaa | +  + |

| size motif | s = aaaaaaaaaa |
|---|---|
| | [a a a a a a a a a a] |
| 2 aa | +  +  +  +  +  +  +  +  +  + |
| 3 aaa | +  +  +  +  +  +  +  +  + |
| 4 aaaa | +  +  +  +  +  +  +  + |
| 5 aaaaa | +  +  +  +  +  +  + |
| 6 aaaaaa | +  +  +  +  +  + |
| 7 aaaaaaa | +  +  +  +  + |
| 8 aaaaaaaa | +  +  +  + |
| 9 aaaaaaaaa | +  +  + |
| 10 aaaaaaaaaa | +  + |

Notice the similarity in the two bases (for s and s'). Irredundant motif of size 6 is missing in the basis for s'. The striking similarity suggests that the general notion of redundancy is perhaps a more natural notion.

Further, every redundant maximal motif of s' can be obtained from its basis using the generating operations. We give some examples for illustration.

a..aa=aaaaa⊕$P^5$(a.aaa.a)⊕$P^5$(aa.aa.aa) and $\mathcal{L}_{a..aa} = \mathcal{L}_{aaaaa} \cup \mathcal{L}_{a.aaa.a} \cup \mathcal{L}_{aa.aa.aa}$.

2. aaa...aa=$P^8$(aaaa..aaaa)⊕$P^8$(aaa.a.aaa) and $\mathcal{L}_{aaa...aa} = \mathcal{L}_{aaaa..aaaa} \cup \mathcal{L}_{aaa.a.aaa}$.

III. Bounding the Irredundant Motifs

Definition 9 (Basis) Given a sequence s on an alphabet $\Sigma$, let m be the set of all maximal motifs on s. A set of maximal motifs $\mathcal{B}$ is called a basis of m if the following hold:

1. for each m∈$\mathcal{B}$, m is irredundant with respect to $\mathcal{B}-\{m\}$, and, 2. let G(X) be the set of all the redundant maximal motifs generated by the set of motifs x, then M=G($\mathcal{B}$).

In general, $|M|=\Omega(2^n)$. The natural attempt now is to obtain as small a basis as possible.

Theorem 1 Let s be a string with n=|s| and let $\mathcal{B}$ be a basis or a set of irredundant motifs (see Definition 8). Then $|\mathcal{B}| \leq 3n$.

Proof The proof is not very straightforward and we begin by giving a few definitions that we use in the argument.

Definition 10 ($\mathcal{L}_a$ straddles $\mathcal{L}_b$) A set $\mathcal{L}_a$ straddles a set $\mathcal{L}_b$ if $\mathcal{L}_a \cup \mathcal{L}_b \neq \phi$, $\mathcal{L}_a - \mathcal{L}_b \neq \phi$ and $\mathcal{L}_b - \mathcal{L}_a \neq \phi$.

Notice that if $\mathcal{L}_a$ straddles $\mathcal{L}_b$, then $\mathcal{L}_b$ straddles $\mathcal{L}_a$.

Let $\mathcal{L}_a=\{1, 2, 3\}$, $\mathcal{L}_b=\{2, 3, 4\}$, $\mathcal{L}_c=\{2, 3\}$ and $\mathcal{L}_d=\{5, 6\}$. Then $\mathcal{L}_a$ straddles $\mathcal{L}_b$.

However $\mathcal{L}_c$ does not straddle any of the others and $\mathcal{L}_d$ does not straddle any of the others.

Definition 11 (sub-motifs of motif m, $S^{[j_1,j_2]}(m)$) Given a motif m, let m[$j_1$], m[$j_2$], ... m[$j_l$] be the l solid characters in the motif m. Then the sub-motifs of m are given as $S^{[j_i,j_k]}(m)$, $1 \leq i < k \leq l$, which is obtained by dropping all the characters before (to the left of $j_i$ and all characters after (to the right of) $j_k$ in m.

For example, let $m_1$=x...yzw..x, $m_2$=xy. Then $S^{[1,10]}(m_1)=m_1$, $S^{[5,10]}(m_1)$=yzw..x, $S^{[5,7]}(m_1)$=yzw, $S^{[6,10]}(m_1)$=zw..x, $S_{[7,10]}(m_1)$=w..x, $S^{[10,10]}(m_1)$=x, and $S^{[2,2]}(m_2)$=y. Notice that $S^{[1,|m'|]}(m)$=m and $|S^{[|m|,|m|]}(m)|$=1. A motif m with |m|=1 is a valid motif by the Definition 3 where the first and last characters are not distinct. In practice, this may not be a useful motif, however we use this in the argument of the proof. Also $\mathcal{L}_{S^{[j_i,|m|]}(m)} \subseteq \mathcal{L}_m+(j_i-1)$.

Consider $\mathcal{B}^*$ ($\mathcal{B} \subseteq \mathcal{B}^*$) where the motifs in $\mathcal{B}^*$ are not maximal and redundant. The idea here is to use the non-maximal motifs m (note that m∉$\mathcal{B}$) in $\mathcal{L}^*$ to count some of the irredundant motifs to which a unique position in s cannot be assigned immediately.

The argument proceeds in two steps.

Step 1. This is the initialization step where we carry out the following:

1. Every position, x∈$\mathcal{L}_{m1}$, $\mathcal{L}_{m2}$, ..., $\mathcal{L}_{ml}$ is assigned ON/OFF with respect to m as follows: If $m_i$, $1 \leq i \leq l$, is such that there exists no $j \neq i$, $1 \leq j \leq l$ so that $\mathcal{L}_{mj} \subset \mathcal{L}_{mi}$ holds, then x is marked ON, otherwise it is marked OFF with respect to $m_i$. We offer and prove the following propositions due to this ON/OFF marking:

Proposition 1 At the end of this step, every motif in that is not redundant, has at least one location x∈$\mathcal{L}_m$ marked ON with respect to m.

Proof. This follows directly from the definition of redundancy. Also a redundant motif m may not have any position marked ON with respect to m. An illustration of this is shown in FIGS. 3A and 3B.

Figure 3A:
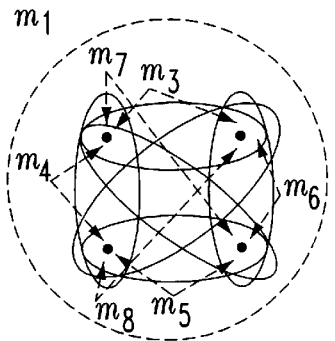
FIGS. 3A and 3B are diagrams illustrating an example of marking of positions with respect to each motif according to one embodiment of the present invention.
Figure 3B:
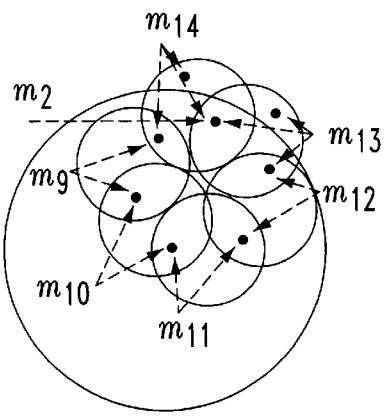

In FIGS. 3A and 3B, an example illustrates the marking of the positions as ON/OFF with respect to each motif. The black dot denotes a position in the location list and the closed curves denote the location list (as a set) of a motif. The locations that are marked ON with respect to a motif are shown by a dashed line segment in the figures. As depicted in FIG. 3A, $m_1$ is a redundant motif since $\mathcal{L}_{m_{m1}} = \mathcal{L}_{m3} \cup \mathcal{L}_{m4} \cup ... \mathcal{L}_{m8}$. Notice that none of the locations can be marked ON with respect to $m_1$. However, as depicted in FIG. 3B, $m_2$ is not redundant and there exists allocation marked ON with respect to $m_2$. Notice that if this position did not exist in its location list, $m_2$ would have been redundant.

Proposition 2 If location x is marked ON with respect to motifs $m_1, m_2, ... m_l$, then every pair of location lists $\mathcal{L}_{mi}$, $\mathcal{L}_{mj}$, i≠j must straddle.

Proof. Assume this does not hold, then $\mathcal{L}_{mi} \subseteq \mathcal{L}_{mj}$, for some i and j. In that case the location x is marked OFF with respect to $m_j$ which is a contradiction.

This is straightforward to see; however, it is the critical property that allows us to proceed further with the argument.

2. For each motif m, define c(m) to be the charge which is a positive integer. This is initialized to 1 for every motif. In the counting process, when there is difficulty in accounting for a motif m, a charge or count for m is assigned at some other motif m': thus m' would account for itself and all the other motifs whose charge it is carrying (thus m' is the banker, as defined in the next step, for all these other motifs).

3. For each motif m, define B(m) to be the banker of m, which is a motif m' that is carrying the charge for m. For each m, initialize B(m)=m.

4. Every motif is marked LIVE/DEAD. At the initialization step, every motif that is not redundant (see Proposition 1 above) is marked LIVE. If there exists a position x that is marked ON with respect to only one LIVE motif m, m is marked DEAD. Repeat this process until no more motifs can be marked DEAD.

In some sense, every DEAD motif at this stage is such that there is a unique position (x of last paragraph), that can be uniquely assigned to it. The number of DEAD motifs≦n.
Step 2. We begin by introducing some more definitions.
Definition 12 (instance) An instance of a motif m is the motif at some location $x \in \mathcal{L}_m$ on the input string s.

For example, let s=abcdabed and let m=ab.d. Then one instance of m on s, shown in bold, is abcdabed and the other instance is abcdabed. The solid characters in the instances of m, shown with a bar, are as. follows: $\overline{abcd}abed$ in the first and $abcd\overline{abed}$ in the second.
Definition 13 (i-connected) An instance of a motif $m_1$ is i-connected to an instance of motif $m_2$ if the two instances have at least i common solid characters.

For example let s=eabcdgeababgd and the motifs are $m_1$=eab..g and $m_2$=ab.d. The first instance of $m_1$ is $\overline{eabcd}$ gexbabgd and the first instance of $m_2$ is $e\overline{abcd}geababgd$ with the solid characters as shown. The two instances are 2-connected since the second (a) and third character (b) in the string are solid characters in the instances of both $m_1$ and $m_2$. The second instance of in is eabcdg$\overline{eababgd}$ and the second instance of $m_2$ is eabcdge$\overline{ababgd}$. These two instances are not 1-connected since they do not share any common solid character, although they share some dot characters.

Let $\overline{m_a}^x$ be an instance of $m_a$ where $x \in \mathcal{L}_{ma}$. To avoid clutter we refer to an instance of motif $m_a$ imply as $\overline{m_a}$.
Lemma 3 Consider an instance each of a set of motifs $m_1$; $m_2, \ldots, m_l$ such that for that instance of $m_i$, the starting position $x \in \mathcal{L}_{mi}$ is marked ON with respect to $m_i$, $1 \leq i \leq l$, and, for every motif $m_i$, there exists a motif $m_j$, $j \neq i$, $1 \leq i, j \leq l$, such that the two instances are 2-connected, then there exist distinct positions $j_1, j_2, \ldots, j_l$ on the input string s, with the corresponding positions, $j'_1, j'_2, \ldots, j'_l$ such that $m_1[j'_1], m_2[j'_2], \ldots, m_l[j'_l]$ are solid characters.

Proof. Assume this does not hold, then there exists instances of motifs $m_{ja}, m_{jb}, 1 \leq j_a, j_b \leq l$ with $m_{jb} \leq m_{ja}$. Consider $m'_{ja}$, the sub-motif of $m_{ja}$ which starts at the starting position on $m_{jb}$ and ends at the ending position of $m_{jb}$. If the position with respect to $m'_{ja}$ is ON, it is a contradiction since then the position at which $m_{jb}$ is incident must be marked OFF. However, if the position with respect to $m'_{ja}$ is OFF, then there exists an instance of $m_{jc}$ such that $m'_{ja} \leq m_{jc}$ and that instance of $m_{jc}$ is marked ON. But $m_{jb} \leq m_{jc}$ and both are ON, which is again a contradiction.

Next, we define an "operational connectedness" on ON-marked instances of LIVE motifs $m_a$ and $m_b$, called the "o-connectedness" which holds if $\overline{m_a}$ is 2-connected to $\overline{m_b}$, or.

2. there exists $\overline{m_c}$, where the instance is ON-marked with respect to LIVE motif $m_c$, and $\overline{m_a}$ is o-connected to $\overline{m_c}$ and $\overline{m_c}$ is o-connected to $\overline{m_b}$.

Lemma 4 o-connectedness is an equivalence relation. Proof. It can be easily verified that o-connectedness is reflexive, symmetric and transitive. Thus, all the ON-marked instances of the LIVE motifs can be partitioned into equivalence classes.

Now, we offer and prove the following proposition.
Proposition 3 Using Lemmas 3 and 4, every instance of a LIVE motif $m_a$ has a solid character at positions associated with it. Let $D(\overline{m_a})=S^{[j_a, |m_a|]}(m_a)$.

Charging Scheme. We next describe a charging (or counting) scheme by which we count the number of motifs. This is best described as an iterative process as follows.

While there exists position x on s such that x is marked ON with respect to LIVE motifs $m_1, m_2, \ldots, m_l$, $l>1$, do the following for $1 \leq i \leq l$:
1. Let $B(m_i)=D(\overline{m_i})$ (see Step 1.3 and Proposition 3);
2. $c(B(m_i))=c(B(m_i))+c(m_i)$ (see Step 1.2).
3. Mark $m_i$ DEAD (see Step 1.4). The only exception is made when $B(m_i)=m_i$. In this case $m_i$ remains LIVE.

We offer and prove the following proposition about the while loop.
Proposition 4 The loop terminates.
Proof. At every iteration at least two distinct LIVE motifs are marked DEAD, hence the loop must terminate.
Proposition 5 At the end of the loop, all the LIVE motifs are such that for every pair $m_i$, $m_j$:

1. $\mathcal{L}_{mi}$ and $\mathcal{L}_{mj}$ do not straddle and

2. $\mathcal{L}_{mi} \subset \mathcal{L}_{mj}$, without loss of generality.

Proof. The first condition holds obviously since otherwise the loop would not terminate since $x \in \mathcal{L}_{mi} \cap \mathcal{L}_{mj}$ would be marked ON with respect to $m_i$ and $m_j$. The second condition also hold obviously since if $\mathcal{L}_{mi} \subset \mathcal{L}_{mj}$ then motif $m_i$ is marked DEAD (Step 1).

Figure 4A:
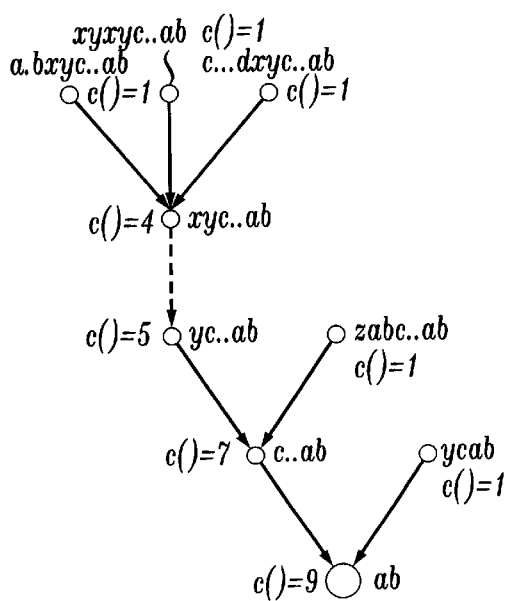
FIGS. 4A and 4B are diagram illustrating examples of assignment of charge to motifs according to one embodiment of the present invention.
Figure 4B:
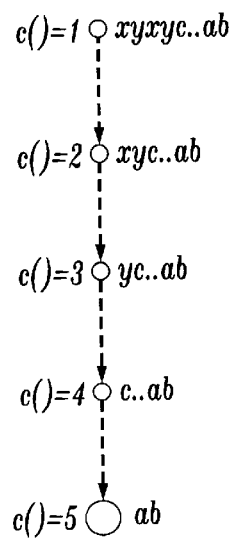

Next, we need to show that the charge c(m) carried by every LIVE motif m at the end of the loop, can be accounted for by $\mathcal{L}_m$. In this context, we make the following observation about the charge: the iterative assignment of charges to a motif has a tree structure. This is best described using an example, as depicted in. FIGS. 4A and 4B . Referring now to FIGS. 4A and 4B, two examples show the different steps in the assignment of charge to motif ab: wherein every level of the tree corresponds to an iteration in the while loop. The dashed edge indicates that the motif at the "to" end of the edge could possibly be non-maximal. Each level of the tree corresponds to an iteration in the loop. For instance, the top level in the left tree (FIG. 4A) denotes that at iteration 1, B(a.bxyc..ab)=B(xyxyc..ab)=B(c...dxyc..ab)=xyc..ab and c(xyc..ab)=1+c(a.bxyc..ab)+c(xyxyc..ab)+c(c...dxyc..ab). At the end of this iteration, motifs a.bxyc..ab, xyxyc..ab and c...dxyc..ab are marked DEAD. At the second iteration, B(xyc..ab)=yc..ab and c(yc..ab)=1+c(xyc..ab) and motif xyc..ab is marked DEAD and so on.
Proposition 6 Let L denote the number of leaf nodes (nodes with no incoming edges) in the charge tree of motif m at the end of the while loop, then $|\mathcal{L}_m| \geq L$. Proof. Such a proposition holds since we know that by our choice of B(.), if $B(m_1)=B(m_2)= \ldots =B(m_l)=m'$ then, by Lemma 3, m' must have l distinct instances, each instance in a distinct equivalent class of motif instances (Lemma 4). However, the instance of m' may not be distinct from each of these instances; hence the non-leaf nodes may not be accounted for but the leaf nodes are. Hence $|\mathcal{L}_m| \leq L$.

At an iteration, if a motif m is charged by more than one motif(or in the charge tree, the node has more than one incident edge), m is certainly maximal. However, if it is charged by exactly one motif then it may or may not be maximal; if it is maximal, it must have an extra instance. We use the following folk-lore lemma to bound the size of I, the number of non-leaf nodes in the charge-tree.
Lemma 5 Given a tree T, where each node, except the leaf nodes, must have at least two children, the number of non-leaf nodes, I is no more than the number of leaf nodes L.

We are not interested in counting non-maximal motifs and these are the only motifs that contribute to a single child for a node in a tree. Thus the number of maximal motifs that were marked LIVE at the start of Step 2 is no more than 2n, using Proposition 6 and Lemma 5.

Using Step 1.4, we have number of maximal and non-redundant motifs$\leq$(n+2n). This concludes the proof of the theorem.

Corollary 1 Given a string s, the basis B is unique. This follows immediately by viewing motifs as location lists and treating these as overlapping sets.

Corollary 2 Given a string s, let M be the set of all maximal (but possibly redundant) motifs which are such that they have only solid characters in them. Then $|M|\leq n$.

Figure 5:
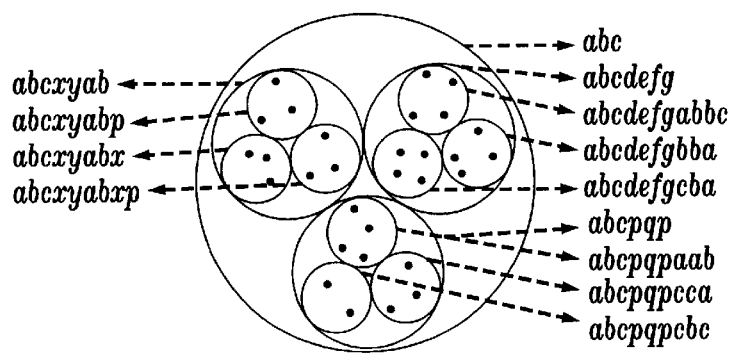
FIG. 5 is a diagram illustrating a relationship between location lists of motifs with no dot characters according to one embodiment of the present invention.

When the motifs are such that they have no dot characters, it can be easily verified that the following hold. For any pair of motifs $m_a$ and $m_b$, 1. $\mathcal{L}_{ma}$ and $\mathcal{L}_{mb}$ do not straddle, and, 2. if a $\mathcal{L}_{ma} \subset \mathcal{L}_{mb}$, then there exist j such that $m_b = m_a[1..j]$. For example $m_a$=abxyz, and $m_b$=ab with j=2. This is illustrated in FIG. 5. Referring now to FIG. 5, an example illustrates the relationship between location lists (as sets) of motifs with no dot characters. Notice that the sets do not straddle and the motif corresponding to a subset of another set is such that the latter is a sub-motif of the former. Thus every redundant motif has a unique solid position associated with it (note that this is not true in the general case).

Using the same arguments for the main theorem, but also counting the redundant motifs, we obtain a bound of n on the total number of maximal motifs.

Corollary 3 Given a strings, let M be the set of all motifs. Let M'⊆M be an arbitrary set of maximal motifs. Then the basis $\mathcal{L}'$ of M' is such that $|\mathcal{B}'|<3n$.

This follows immediately since the proof of the theorem does not use the fact that M is the set of all motifs of s. It simply works on the location lists (sets) of this special set of maximal motifs.

IV. Algorithm to Detect the O(n) Irredundant Motifs

The next natural question is whether the irredundant maximal motifs can be detected in polynomial time. We present the following iterative algorithm to accomplish this goal. The input parameters are: s, a string on some alphabet Σ and integer k. Each motif must appear at least k times in s.

1. Construct all the motifs with exactly two solid characters. Let the set of these motifs be M, then $|M|\leq|\Sigma|^2 n$. Construct a graph with every vertex $v_m$ corresponding to a motif m and a directed edge exists from $v_{mp}$ to $v_{mc}$ if $\mathcal{L}_{mc} \subseteq \mathcal{L}_{mp}$ (or $m_p \leq m_c$).

2. For every vertex $v_{mp}$, consider the vertices incident on all the outgoing edges $v_{mc1}, v_{mc2}, \ldots, v_{mcl}$. If $\mathcal{L}_{mp} = \mathcal{L}_{mc1} \cup \ldots \cup \mathcal{L}_{mcl}$, then we do the following.
   (1) Case l=1:
   Remove the vertex $v_{mc1}$ and replace the associated motif $m_p$ of vertex $v_{mp}$ with $m=m_p \hat{\times} m_{c1}$.
   (2) Case l>1:
   Remove the vertex $v_{mp}$ and all its incident edges (since this is a redundant motif).

3. Define a pair of motifs $m_a$ and $m_b$ to be compatible if $m_a[|m_a|]\leq m_b[1]$ holds. For every pair of compatible motifs $m_i, m_j$ (corresponding to vertices in the graph), let $\mathcal{L}'_{mi} = \mathcal{L}_{mi} + |m_i|$. Construct $\mathcal{L}'_{mi} \cap \mathcal{L}_{mj} = \mathcal{L}_{mnew}$. Construct $m_{new}$, if there exist compatible motifs $m_i$ and $m_j$ with $(\mathcal{L}_{mi}+|m_i|-1) \cup \mathcal{L}_{mj} = \mathcal{L}$mnew and $|\mathcal{L}_{mnew}|\geq k$. Motif $m_{new}$ is obtained by concatenating the compatible motifs $m_i$ and $m_j$: $m_{new}=m_i+m_j$. For example if $m_i$=ab..d and $m_j$=d.e.ac, then $m_{new}$=ab..d.e.ac.

Update the graph as follows.
(a) Introduce a vertex corresponding to motif $m_{new}$
(b) Introduce a directed edge from $v_{mi}$ to $vm_{new}$.

4. Repeat Steps 2 and 3 until $\mathcal{L}_{mnew}=\{\ \}$, for every pair of compatible motifs $m_i, m_j$ with $m_{new}=m_i+m_j$.

The following is a proof of correctness of the algorithm.

Lemma 6 Let M be all the motifs produced by the algorithm. Then M=B, the basis set. Proof. Let ($\mathcal{B}$) be the set of all the redundant maximal motifs generated by $\mathcal{B}$ and let G(M) be the set of all the redundant maximal motifs generated from M. We need to show G($\mathcal{B}$)=G(M).

Let m∈G(M), then clearly m∈G($\mathcal{B}$) since all the motifs produced by the algorithm are maximal motifs due to pruning at Step 2 of the algorithm and see Lemma 8 about enumerating G( ). Thus G(M)⊆G($\mathcal{B}$).

Let m∈G($\mathcal{L}$). Let us assume the contrary, that is, m∉G(M).

1. Case 1: m is not redundant.

We make the following straightforward observations about the algorithm. Proposition 7 Let the algorithm produce the set of motifs M in p iterations. For every motif $m_a$ on the input s, there exist motifs $m_a^1, m_a^2, \ldots, m_a^p = m_a$ at each iteration respectively such that the following hold:

(a) $m_a^{i+1} = m_a^i + m'_a$, for some motif $m'_a$ or an empty string and (b) $\mathcal{L}ma^1 \supseteq \mathcal{L}m_a^2 \supseteq \ldots \supseteq \mathcal{L}m_a^p$ At the very first iteration (Step 1 of the algorithm) the algorithm produces all the largest possible location lists, assuming that the motif m of interest has $|m|\geq 2$ (however, if it requires $|m|\geq 1$, at this first step we produce all the motifs of size one or single character motifs and "grow" them appropriately in the algorithm). In other words, there exists no motif $m_{queer}$ such that $\mathcal{L}_{mqueer} \supset \mathcal{L}_{mb}$ where $m_b$ is produced in Step 1. Hence there must exist $m_k$ such that $\mathcal{L}_{mk} \supset \mathcal{L}_m$ and $m_k$ was pruned as a redundant motif (Step 2.2 of the algorithm) at some iteration $i_l$. Also $m=m_k+m'$ for some motif m'. If m' is an empty string, $m=m_k$ which is redundant and that is a contradiction.

By Proposition 7, there must exist $m^{i1}$ corresponding to m' at the end of iteration $i_l$. If $m_{i1}$ is redundant, it leads to a contradiction since then m is also redundant. Consider the case when $m^{i1}$ is not redundant. Then the algorithm must "concatenate" (Step 3 of the algorithm) compatible motifs $m_k$ and $m^{i1}$ at iteration $i_1$ to produce $m_b$ at the next iteration with $\mathcal{L}m \subseteq \mathcal{L}m_b \subseteq \mathcal{L}m_k$, which is again a contradiction by the choice of $m_k$ at iteration $i_1$.

Hence m∈G(M).

2. Case 2: m is redundant.

Then there exist motifs $m_1, m_2, \ldots, m_l$, each of which is not redundant that renders m redundant. By using Case 1, we can show that each of $m_1, m_2, \ldots, m_l$ must be in G(M). Hence in must be in G(M).

Also, it is easy to see that all the motifs in M are maximal and mutually irredundant due to the pruning at Step 2. Thus, by Corollary 1, M is the basis set. This concludes the proof. Lemma 7 The algorithm takes $O(n^3 \log n)$ time. Proof. The point to note here is that the nodes in the graph or the motifs being constructed do not grow exponentially. At the very first iteration there are O(n) motifs (Step 1) and at the end of Step 2, there are again O(n) motifs, using Corollary 3. Thus, there are $O(n^2)$ comparisons made at each iteration. Since the location list can be no more that n, the amount of work done is $O(n^3 I)$, where I is the number of iterations. But $I=\log L$ where L is the maximum number of solid characters in a motif, since the motif grows by concatenating two smaller motifs. But L<n, hence the result.

Figure 6:
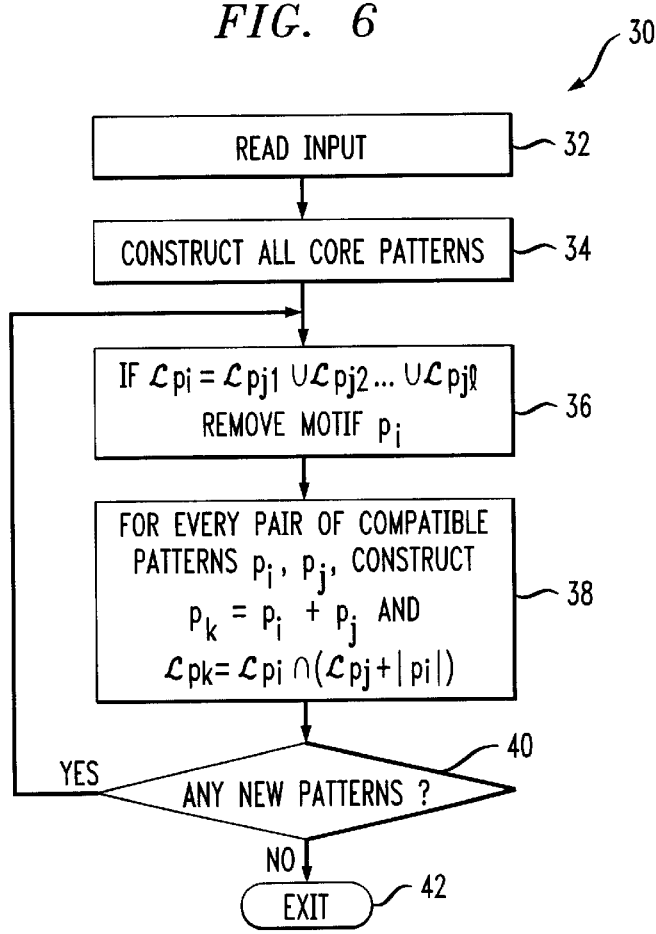
FIG. 6 is a flow diagram illustrating a motif discovery methodology according to one embodiment of the present invention.

Given the above described algorithm, FIG. 6 depicts a flow chart representation of the inventive algorithm. It is to be appreciated that such an irredundant motif detection methodology may be implemented in the motif discovery/generation module 12 (FIG. 1). Thus, the illustrative methodology 30 according to the present invention comprises the following steps. In step 32, the input data sequence or sequences to be processed are read. This may be from a source database (e.g., database 14 in FIG. 1) or directly from a user. In step 34, all core patterns are constructed and associated location lists are generated. Step 34 corresponds to Step 1 in the above-described algorithm. It is to be appreciated that while the algorithm above provides for constructing all the motifs with exactly two solid characters, the invention is not so limited. It is to be appreciated that the number of solid characters in the core patterns is a constant and is not a function of the size n of the input sequence. Thus, the core patterns may be constructed with less or more than two solid characters or elements. Also, a pattern may include any number of don't care positions or dot characters.

Next, in step 36, an intelligent pruning operation is performed. That is, $\mathcal{L}_{pi}=\mathcal{L}_{pj}1 \cup \mathcal{L}_{pj}2 \ldots \cup \mathcal{L}_{pj}l$, then we remove motif $p_i$. That is, we remove a pattern from the set when the location list of that pattern is the union of the location lists of at least two other patterns in the set. Step 36 corresponds to Step 2 in the above-described algorithm.

In step 38, for every pair of compatible patterns $p_i$, $p_j$, we construct a motif $p_k$ which is defined as $p_i+p_k$ and location list $\mathcal{L}_{pk}$ equal to $\mathcal{L}_{pi} \cap (\mathcal{L}_{pj}+|p_i|)$. That is, for each pair of compatible patterns in the set, a new pattern is constructed which is a concatenation of the pair of compatible patterns. An associated location list is also generated for each new pattern. It is to be appreciated that the term "compatible" may have a different meaning depending on the type of data in the input data sequence. Compatibility (denoted herein as "<") is defined for various input data sequence types in Definitions 1, 14 and 16. Note that step 38 corresponds to Step 3 in the above-described algorithm.

Then, in step 40, it is determined whether any additional patterns are present. If so, steps 36 and 38 are repeated. If not, the process ends (block 42). Step 40 corresponds to Step 4 in the above-described algorithm.

V. Generating Redundant Motifs: Annotated Trie

The last section describes a polynomial time algorithm to produce the unique basis set $\mathcal{B}$ for a string s. The elements of $\mathcal{B}$ are maximal and not redundant. However, it is possible that there exist applications where the user requires all the motifs—either non-maximal or redundant, or, both. For such applications, we present an efficient and systematic way of generating non-maximal or redundant motifs or both by storing the motifs in $\mathcal{B}$ in a trie structure, that is suitably annotated to produce the location lists. The trie structure is well known in the art and is described, for example, in A. V. Hoe et al., "Data Structure and Algorithms," Addison-Wesley Publishing Company, 1983, the disclosure of which is incorporated herein by reference. This procedure will implicitly use the generating operators described in Section II(a) above. It is to be understood that other redundant motif generation techniques may be employed.

It is to be appreciated that such a redundant motif generation methodology may be implemented in the motif discovery/generation module 12 (FIG. 1) along with the irredundant motif detection methodology described above. Thus, after both methodologies are performed, the resulting motifs are stored in motif store 16 (FIG. 1) for use by an application 18 (FIG. 1).

Figure 7:
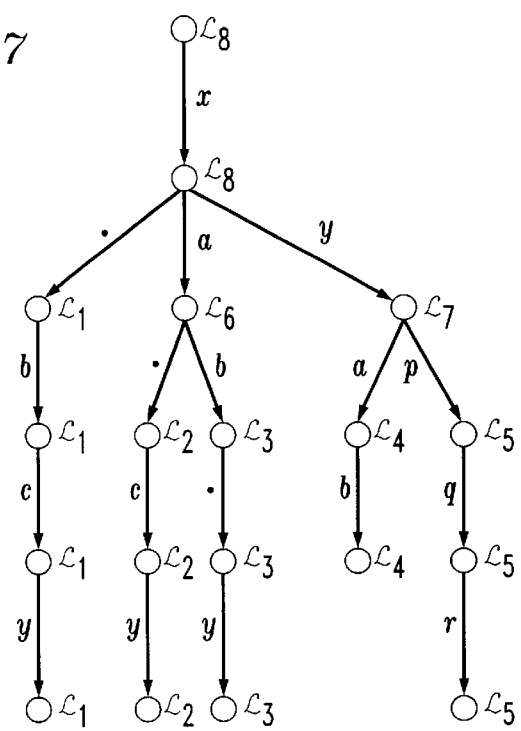
FIG. 7 is a diagram illustrating an annotated trie corresponding to maximal and non-redundant motifs according to one embodiment of the present invention.

In this illustrative redundant motif generation methodology, we store the motifs of the basis $\mathcal{B}$ in a trie structure as shown in FIG. 7. Particularly, FIG. 7 shows an annotated trie corresponding to maximal and non-redundant motifs x.bcy, xa.cy, xab.y, xyab, xypqr. Each leaf node of this edge-labeled trie is annotated with the location lists as shown: $\mathcal{L}_1=\mathcal{L}_{x.bcy}$, $\mathcal{L}_2=\mathcal{L}_{xa.cy}$, $\mathcal{L}_3=\mathcal{L}_{xab.y}$, $\mathcal{L}_4=\mathcal{L}_{xyab}$, $\mathcal{L}_5=\mathcal{L}_{xypqr}$, $\mathcal{L}_6=\mathcal{L}_2 \cup \mathcal{L}_3$, $\mathcal{L}_7=\mathcal{L}_4 \cup \mathcal{L}_5$, $\mathcal{L}_8=\mathcal{L}_1 \cup \mathcal{L}_6 \cup \mathcal{L}_7$. This trie is annotated with the location lists so that every redundant motif can be read off the trie along with the location list. The data structure ensures that the redundant motifs can be obtained in time linear with respect to the output. The algorithm is relatively straightforward and we describe it below.

For each path (reading off the labels on the edges $P_1$ from the root node of the trie $\sigma s_1 s_2 \ldots s_l$, $\sigma \in \Sigma$, $s_i \in \Sigma + \{.\}$ For each distinct and longest path $P_2$ (this means that the path cannot be grown any further without having to make a choice from alternate paths) from the root node, $\sigma s'_1 s'_2 \ldots$, $s'_k$, $s'_i \in \Sigma + \{.\}$, satisfying the following:

(a) $n \leq l$,
(b) $s'_k = s_k \in \Sigma$ (since the last character of a valid motif must be a solid character), and
(c) either $s_i = s'_i$ or one of them is the dot character.

1. Let $m_1 = \sigma s_1 s_2 \ldots s_k$ and $m_2 = \sigma s'_1 s'_2 \ldots s_k$. Construct $m_{new} = m_1 \oplus m_2$. Further, $\mathcal{L}_{new} = \mathcal{L}_1 \cup \mathcal{L}_2$ where $\mathcal{L}_1$ is the annotation at the node with the incoming edge labeled with $s_l$ and similarly $\mathcal{L}_2$. Notice that this is the generating operator as defined in Section II(a) above and when n<l, the prefix operator has been implicitly used on $m_2$.
2. Project $m_{new}$ onto the trie updating the new node with $\mathcal{L}_{new}$.

Figure 8A:
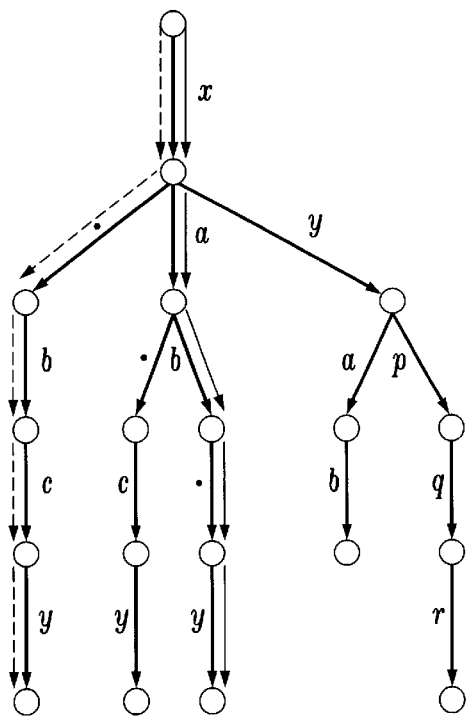
FIGS. 8A and 8B are diagrams illustrating an example of construction of redundant motifs from the trie of basis motifs.
Figure 8B:
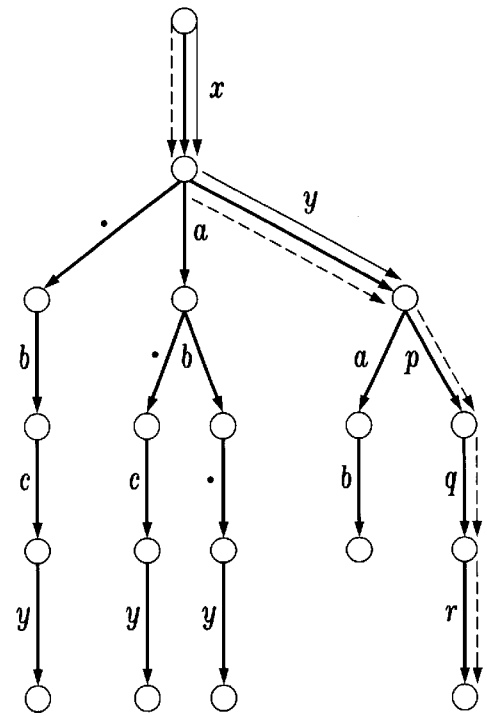

FIGS. 8A and 8B depict an illustration of the algorithm. In FIGS. 8A and 8B, an example shows the construction of the redundant motifs from the trie of the basis motifs. $P_1$ is shown by a dashed solid line and $P_2$ is shown by solid line superimposed on the trie of the previous figure. In the first case $P_1$=x.bcy and $P_2$=xab.y giving the new motif x.b.y. In the second case $P_1$=xypqr, $P_2$=xy giving the new motif xy and the associated location list is $\mathcal{L}_7$. Note that in the latter case, $P_2$ can be extended in at least two ways (that may or may not be compatible with $P_1$).

We make the following claim about the algorithm.

Lemma 8 The algorithm produces all maximal redundant motifs. Proof. It is easy to see that the motif is maximal since $P_2$ is the longest compatible (so that the binary operator $\oplus$ is valid) path.

Next, we show that all the maximal and redundant motifs are generated. Any redundant motif m can be generated from $m_1, m_2, \ldots, m_l \in \mathcal{B}$ for some l>1. But the binary operator $\oplus$ is commutative and associative and the unary prefix operator $P^\delta(\ )$ distributes over the binary operator (see Section II(a)). Thus, although we consider only pairwise paths in the algorithm (for ease of implementation), the new motif is projected onto the trie and this process can be successively used to obtain m.

VI. Generalization

In this section we present two generalizations of the pattern discovery problem, one on sequence of character sets and the other derives its elements from a continuous domain.

(a) Character-set Range

For the sake of brevity, let us call the problem defined in Section I as a "discrete-singleton" problem. In this section, we explore the problem of finding patterns on an input that is a sequence of sets instead of characters. Let us call this set of problem as the "discrete-set" problem. The discrete-singleton problem can be viewed as a special case of the discrete-set problem where each character of the input is a singleton set. There is a natural extension of the notion of motifs on such inputs as is illustrated in the following examples.

Let the input be s=[abc]defad[eg]f. For this input the alphabet set is {a, b, c, d, e, f, g}. The first position has three elements a, b, c in the set; the second is a singleton d, the third is a singleton e and so on. A 2-motif m (that occurs at least two times in s) is m=adef with $\mathcal{L}_m=\{1, 5\}$. Notice that a=m[1]∈s[1], d=m[2]∈s[2] and so on.

Let s=[abc]def[ab]a[eg]f. Then, a 2-motif m=[ab].ef. Also, $m_1$=a.ef and $m_2$=b.ef are two motifs, but $m_1, m_2 \leq m$ and $\mathcal{L}m_1 = \mathcal{L}m_2 = \mathcal{L}m$, $m_1$ and $m_2$ are not maximal with respect to m by the definition of maximality.

We simply need to define the partial order here as done in Definition 1 for the discrete-singleton problem.

Definition 14 ($\sigma_1 <, =, \leq \sigma_2$) If $\sigma_1$ is a "don't care" character then $\sigma_1 < \sigma_2$. If $\sigma_1 \subseteq \sigma_2$ then $\sigma_1 = \sigma_2$. If either $\sigma_1 < \sigma_2$ or $\sigma_1 = \sigma_2$ holds, then $\sigma_1 \leq \sigma_2$.

The notion of maximality and redundancy are identical to the earlier case (Section I, Section II) using the partial order defined here.

We have the following result for the discrete-set problem.

Theorem 2 Given an alphabet Σ, let s be a string on the power set of Σ with n=|s|. Let $\mathcal{B}$ be the set of maximal irredundant motifs on s. Then $\mathcal{B}$ is unique and $|\mathcal{B}| \leq 3n$. Also, there exists a $O(n^3 \log n)$ algorithm to detect $\mathcal{B}$.

The proof is exactly along the lines of the theorem 1. The algorithm in Section IV has been defined in terms of iterative intersection of location lists, thus extends in a straightforward manner to the discrete-set problem. However, in the very first step, $|M| \leq 2^{2|\Sigma|}n$.

(b) Continuous Range

In this section we consider the problem of detecting patterns on a sequence of real numbers. We call this the continuous problem. Here we have to use a given $\delta/2 \geq 0$ for equality of two numbers, i.e., two numbers x and y are equal if and only of $|x-y| \leq \delta/2$.

Again, we simply need to define the partial order in this case, and all the other definitions follow naturally.

Definition 15 ($\sigma_1, =, \sigma_2$) If $\sigma_1$ is a "don't care" character then $\sigma_1 < \sigma_2$. If $|\sigma_1 - \sigma_2| \leq \delta/2$, for a given $\delta/2$, then $\sigma_1 = \sigma_2$. If either $\sigma_1 < \sigma_2$ or $\sigma_1 < \sigma_2$ holds, then $\sigma_1 \leq \sigma_2$.

For example, let s=0.65 3.6 2.2 0.75 2.1 2.2 0.80 6.1 2.2 with $\delta/2$=0.5. What are the motifs for this input? Some possible motifs are: $m_1$=0.66. 2.2 with $\mathcal{L}_{m1}=\{1, 4, 7\}$, $m_2$=0.67. 2.2 with $\mathcal{L}_{m2}=\{1, 4, 7\}$, $m_3$=0.68. 2.2 with $\mathcal{L}m_3=\{1, 4, 7\}$. In fact there are uncountably infinite motifs. To circumvent this problem, we will allow the motifs to draw there alphabets not just from real numbers but closed real intervals. For example, for the above problem consider the following three motifs using real intervals: $m_1^b$=(0.55, 0.90).2.2 with, $\mathcal{L}m_1^b=\{1, 4, 7\}$. $m_2^b$=(0.50, 0.90).2.2 with $\mathcal{L}m_2^b=\{1, 4\}$ and $m_3^b$=(0.55, 1.0).2.2 with $\mathcal{L}m_3^b=\{4, 7\}$. Motifs $m_1, m_2, m_3$ and uncountably infinite motifs are represented in $m_1^b$.

To incorporate the real intervals in the alphabet of the motifs, we extend the partial order definition 15 as follows.

For the rest of the discussion let a real number x be the closed interval [x, x].

Definition 16 ($\sigma_1 <, =, \leq \sigma_2$) If $\sigma_1$ is a "don't care" character then $\sigma_1 < \sigma_2$. If for all x∈$\sigma_1$, and for all y∈$\sigma_2$, and $|x-y| \leq \delta/2$, then $\sigma_1 = \sigma_2$. If either $\sigma_1 = \sigma_2$ or $\sigma_1 = \sigma_2$ holds, then $\sigma_1 \leq \sigma_2$.

By this definition, $m_1, m_2, m_3 \leq m_1^b$, with $\mathcal{L}m_1 = \mathcal{L}m_2 = \mathcal{L}m_3 = \mathcal{L}m_1^b$, thus $m_1, m_2, m_3$ are non-maximal with respect to $m_1^b$.

Theorem 3 Given an instance of the continuous problem on a an input string s with |s|=n, there exists a polynomial time reduction to an instance of the discrete-set problem on s' with |s'|=n.

Proof. Given a closed interval [a, b], let $S^{[a,b]}$ denote all the elements $s[i_1], s[i_2], \ldots, s[i_p]$ such that $s[i_j] \leq [a, b] 1 \leq j \leq p$.

Let L=min {s[1], s[2], ..., s[n]} and U=max {s[1], s[2], ..., s[n]}. Obtain a minimum number of intervals l given as $[L=x_{11}, x_{12}], [x_{21}, x_{22}], \ldots, [x_{l1}, x_{l2}=U]$ that satisfy the condition that $S^{[xj1,xj2]} \neq S^{[xk1,xk2]}$ for distinct j and k.

It is easy to show the following.

Proposition 8 $l \leq n$.

Proof. If $s[i_1], s[i_2], \ldots, s[i_p] \leq [a, b]$, then there does not exist a distinct $i_x$ (distinct from $i_1, i_2, \ldots, i_p$), such that $s[i_l] < s[i_x] < s[i_p]$ and $s[i_x] \leq [a, b]$. Thus given an ordering of numbers the maximum number of subsets of these numbers such that if numbers $x_i, x_j$ belong to a subset S then for all $x_k$ with $x_i < x_k < x_j$, $x_k \in S$, is at most n.

Now, we transform s of real numbers to s' on an alphabet set $\sigma_1, \sigma_2, \ldots, \sigma_l$ in polynomial time as follows: If s[i]∈ $S^{[i_11,i_12]}, S^{[i_21,i_22]}, \ldots, [i_{p1},i_{p2}]$, then $s'[i]=[\sigma_{i1}, \sigma_{i2} \ldots, \sigma_{ip}]$. Thus the alphabet size is l for s'. The solution for the continuous problem can be constructed from that of the discrete-set problem as follows. Let m' be a motif on s', then m, a motif on s, is constructed as follows. m[i]='.', if m'[i]='.'. If m'[i]=$[\sigma_{i1}, \sigma_{i2}, \ldots \sigma_{ip}]$, then m[i]=$S^{[i_11,i_12]} \cup [i_21,i_22] \cup \ldots \cup S^{[i_{p1},i_{p2}]}$. It is straightforward to see that $\mathcal{L}_{m'} = \mathcal{L}_m$, i.e., if m' occurs at position j on s', then in occurs at position j on s. This concludes the proof.

Theorem 4 Given a string of real numbers s with |s|=n, and $0 < \delta/2$, let $\mathcal{B}$ be the set of maximal irredundant motifs on s. Then $\mathcal{B}$ is unique and $|\mathcal{B}| \leq 3n$. Also, there exists an $O(n^3 \log n)$ algorithm to detect $\mathcal{B}$. This follows directly from theorems (2) and (3).

VII. Applications

In this section we give some examples of possible applications of the results of the preceding sections. However, one of ordinary skill in the art will realize many other applications given the inventive teachings provided herein.

(a) Association Rules

The present invention may be applied to solves an important problem in the context of data mining which has been addressed in exiting literature, e.g., R. Agrawal eta al. "Advances in Knowledge Discovery and Data Mining," chapter 12, In Fast Discovery of Association Rules, AAAI/MIT Press, MA, 1995.

Definition 17 (k-association rule) Given n transactions (or records) each with F fields. Each of the field $f_j$, $1 \leq j < F$, takes one of $d^j$ discrete values. A two tuple (f, $v_f$) denotes the assignment of the value $v_f$ to the field f. An association rule or a pattern r, is a collection of two tuples that hold in at least k transactions, given a positive integer k. $\mathcal{L}_r$ is the set of transactions in which r holds.

r is maximal if and only if there exists no other association rule r' such that r⊂r' and $\mathcal{L}_r \subseteq \mathcal{L}_{r'}$.

It is straightforward to see that the problem of extracting all maximal k-association rules from n transactions with F fields can be mapped onto a special case of discovering k-motifs from a string of size nF. This string can be defined by fixing the order of fields in a transaction and considering only the values each field takes. In this context we can introduce the notion of "irredundant k-association rules." In a strict sense, the total number of maximal k-association rules can be no more than $2^{dF}$ where the F fields take d values, which for the purposes of complexity analysis is only a constant (!) unless d or F is a function of n. However, for practical purposes this number may be considered extremely large. In this context, it might be economical to use the notion of irredundancy to cut down the large number of rules by using a suitable modification of the algorithm of Section IV. All the redundant k-association rules any ways can be constructed from the basis set.

(b) Multiple Sequence Alignment

Another useful application is alignment of multiple sequences based on motif discovery. It can be shown that irredundant motifs give the same best alignment as that of all maximal motifs and, since their number is only polynomial as opposed to exponential, it offers validity to this approach. See, e.g., L. Parida et al., "An approximation algorithm for alignment of multiple sequences using motif discovery," Journal of Combinatorial Optimization, 1999; and L. Parida et al., "MUSCA: An algorithm for constrained alignment of multiple data sequences," Genome Informatics, no. 9:112–119, 1999, the disclosures of which are incorporated herein by reference.

(c) Further Examples

Here we give a few interesting examples that help with further understanding of motifs.

EXAMPLE 3

We give the following example to show that the number of maximal motifs (not necessarily irredundant) is large even if we restrict the motifs to have no more than a small number of dot characters, d between two solid characters.

Let d=1. Consider the input string in Example 1. We construct a new motif by placing a new character Z between every two characters as follows:

$aZc_1Zc_2Zc_3ZbaZXZc_2Zc_3ZbYaZc_1ZXZc_3ZbYYaZc_1Zc_2ZXZb$

The length of the string just doubles, at most whereas the number of maximal motifs, that have no more than one consecutive dot character is at least as many as it was before.

EXAMPLE 4

We give the following example to show that a redundant motif can be constructed in at least two distinct ways from different sets of maximal motifs. Consider the input following string:

XbcY XbdY XedY XecY

Let $m_1$=Xb.Y with $\mathcal{L}_{m1}$={1,5}, $m_2$=X.dY with $\mathcal{L}_{m2}$={5; 9}, $m_3$=Xe.Y with $\mathcal{L}_{m3}$={9, 13}, $m_4$=X.cY with $f_4$={1,13}.

Notice that $\mathcal{L}_{m1} \cup \mathcal{L}_{m3} = \mathcal{L}_{m2} \cup \mathcal{L}_{m4} = \mathcal{L}_m$, where m=X..Y. Thus, m can be constructed either from $m_1$ and $m_3$ or from $m_2$ and $m_4$.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method of detecting repeating patterns in an input data sequence, wherein the data sequence includes elements from an element alphabet, the method comprising the steps of:

obtaining the input data sequence;

constructing a set of patterns from the input data sequence, each pattern being unique and including one or more elements from the input data sequence, and each pattern having a list associated therewith representing the location of the pattern in the input data sequence;

removing a pattern from the set when the location list of the pattern is a union of the location lists of at least two other patterns in the set;

for each pair of compatible patterns in the set, constructing a new pattern which is a concatenation of the pair of compatible patterns, each new pattern having a location list associated therewith; and storing the patterns, and associated location lists, remaining after the removing step and the new pattern constructing step as the detected repeating patterns.

2. The method of claim 1, wherein one or more patterns further include one or more don't care positions.

3. The method of claim 1, wherein the elements of the input data sequence are characters.

4. The method of claim 1, wherein the elements of the input data sequence are character sets.

5. The method of claim 1, wherein the elements of the input data sequence are real numbers.

6. The method of claim 1, wherein no more than 3n repeating patterns are detected given an input data sequence which includes n elements.

7. The method of claim 1, wherein the first constructing step further comprises constructing the unique patterns with at least two elements such that the cardinality of the set of patterns is less than or equal to the square of the cardinality of the element alphabet multiplied by the number of elements in the input data sequence.

8. The method of claim 7, further comprising the step of constructing a graph having vertices and directed edges wherein each vertex $v_m$ corresponds to a pattern m and a directed edge exists from $v_{mp}$ to $v_{mc}$ if $\mathcal{L}_{mc} \subseteq \mathcal{L}_{mp}$ where $\mathcal{L}$ represents a location list.

9. The method of claim 8, wherein the removing step further comprises, for each vertex $v_{mp}$, considering the vertices incident on outgoing edges $v_{mc1}, v_{mc2}, \ldots, v_{mcl}$, and when $\mathcal{L}_{mp}$ is equivalent to unions of $\mathcal{L}_{mc1}$ through $\mathcal{L}_{mcl}$, then:

removing the vertex $v_{mc1}$ and replacing the associated pattern $m_p$ of vertex $v_{mp}$ with a union of $m_p$ and $m_{cl}$, when l is equivalent to one; and removing the vertex $v_{mp}$ and its incident edges, when l is greater than one.

10. The method of claim 9, wherein the second constructing step further comprises:

defining a pair of patterns $m_a$ and $m_b$ to be compatible when the last character in $m_a$ is equivalent to the first character in $m_b$;

for each pair of compatible patterns $m_i$, $m_j$, corresponding to vertices in the graph, letting $\mathcal{L}'_{mi}$ be equivalent to the sum of $\mathcal{L}_{mi}$ and the length of pattern $m_i$;

constructing $\mathcal{L}_{mnew}$ to be equivalent to the intersection of $\mathcal{L}'_{mi}$ and $\mathcal{L}_{mj}$; and constructing pattern $m_{new}$ when there exist compatible patterns $m_i$ and $m_j$ such that the union of: (i) the sum of $\mathcal{L}_{mi}$ and the length of pattern $m_i$ minus one; and (ii) $\mathcal{L}_{mj}$, is equivalent to $\mathcal{L}_{mnew}$, and the cardinality of $\mathcal{L}_{mnew}$ is greater than or equal to a value k.

11. The method of claim 10, further comprising the step of updating the graph by introducing a vertex corresponding to pattern $m_{new}$ and introducing a directed edge from $v_{mi}$ to $vm_{new}$.

12. The method of claim 11, repeating the removing step and the new pattern constructing step until $\mathcal{L}_{mnew}$ is empty, for every pair of compatible patterns $m_i$, $m_j$ with $m_{new}$ equivalent to the union of $m_i$ and $m_j$.

13. The method of claim 1, wherein the stored patterns are maximal and non-redundant.

14. The method of claim 13, further comprising the step of generating patterns, from the stored patterns, which are at least one of non-maximal and redundant.

15. The method of claim 14, further comprising the step of storing the at least one of non-maximal and redundant patterns.

16. The method of claim 14, wherein the at least one of non-maximal and redundant patterns are generated in accordance with one or more annotated tries.

17. The method of claim 1, wherein the input data sequence is a protein sequence.

18. The method of claim 17, wherein the stored patterns are used in accordance with protein sequence homology detection.

19. The method of claim 1, wherein the input data sequence is obtained from a client device via a network and the first constructing step, the removing step, the second constructing step and the storing step are performed in accordance with a server coupled to the network.

20. Apparatus for detecting repeating patterns in an input data sequence, wherein the data sequence includes elements from an element alphabet, the apparatus comprising:

at least one processor operative to: (i) obtain the input data sequence; (ii) construct a set of patterns from the input data sequence, each pattern being unique and including one or more elements from the input data sequence, and each pattern having a list associated therewith representing the location of the pattern in the input data sequence; (iii) remove a pattern from the set when the location list of the pattern is a union of the location lists of at least two other patterns in the set; (iv) for each pair of compatible patterns in the set, construct a new pattern which is a concatenation of the pair of compatible patterns, each new pattern having a location list associated therewith; and (v) store the patterns, and associated location lists, remaining after the removing operation and the new pattern constructing operation as the detected repeating patterns.

21. An article of manufacture for detecting repeating patterns in an input data sequence, wherein the data sequence includes elements from an element alphabet, comprising a machine readable medium containing one or more programs which when executed implement the steps of:

obtaining the input data sequence;

constructing a set of patterns from the input data sequence, each pattern being unique and including one or more elements from the input data sequence, and each pattern having a list associated therewith representing the location of the pattern in the input data sequence;

removing a pattern from the set when the location list of the pattern is a union of the location lists of at least two other patterns in the set;

for each pair of compatible patterns in the set, constructing a new pattern which is a concatenation of the pair of compatible patterns, each new pattern having a location list associated therewith; and storing the patterns, and associated location lists, remaining after the removing step and the new pattern constructing step as the detected repeating patterns.

* * * * *